United States Patent
Trutwig et al.

(10) Patent No.: US 10,357,580 B2
(45) Date of Patent: Jul. 23, 2019

(54) ELECTRODE ARRANGEMENT FOR FORMING A DIELECTRIC BARRIER PLASMA DISCHARGE

(71) Applicant: CINOGY GMBH, Duderstadt (DE)

(72) Inventors: Leonhard Trutwig, Duderstadt (DE);
Mirko Hahnl, Berlingerode (DE);
Karl-Otto Storck, Duderstadt (DE);
Matthias Kopp, Gieboldehausen (DE);
Annika Schaefer, Goettingen (DE);
Dirk Wandke, Heilbad Heiligenstadt (DE)

(73) Assignee: CINOGY GmbH, Duderstadt (DE)

( * ) Notice: Subject to any disclaimer, the term of this patent is extended or adjusted under 35 U.S.C. 154(b) by 231 days.

(21) Appl. No.: 15/505,960

(22) PCT Filed: Aug. 25, 2015

(86) PCT No.: PCT/DE2015/000422
§ 371 (c)(1),
(2) Date: Feb. 23, 2017

(87) PCT Pub. No.: WO2016/037599
PCT Pub. Date: Mar. 17, 2016

(65) Prior Publication Data
US 2018/0221517 A1    Aug. 9, 2018

(30) Foreign Application Priority Data

Sep. 11, 2014    (DE) .................. 10 2014 013 716

(51) Int. Cl.
*A61B 18/04* (2006.01)
*A61L 2/00* (2006.01)
(Continued)

(52) U.S. Cl.
CPC .......... *A61L 2/0011* (2013.01); *A61B 18/042* (2013.01); *A61L 2/14* (2013.01);
(Continued)

(58) Field of Classification Search
CPC ... A61B 18/042; H05H 1/2406; A61L 2/0011; H01J 37/00
See application file for complete search history.

(56) References Cited

U.S. PATENT DOCUMENTS

2006/0042545 A1* 3/2006 Shibata ............. H01J 37/32009
                                                    118/722
2012/0259270 A1* 10/2012 Wandke ............... A61N 1/0408
                                                    604/23
(Continued)

FOREIGN PATENT DOCUMENTS

DE          102 03 543 A1    10/2003
DE    11 2004 000 057 B4     9/2008
(Continued)

OTHER PUBLICATIONS

J. Roth, Industrial Plasma Engineering vol. 2: Applications to Nonthermal Plasma Processing, 2001, pp. 122-125, Institute of Physics Publishing.

*Primary Examiner* — Jaymi E Della
*Assistant Examiner* — Rachel A. Vierra
(74) *Attorney, Agent, or Firm* — W & C IP

(57) ABSTRACT

An electrode arrangement for forming a dielectric barrier plasma discharge between a flat surface (4) of the electrode arrangement and a surface to be treated which functions as a counter surface and on which a fluid can collect, comprising a flat electrode (14) which can be connected to a high-voltage source by means of a connector and which is completely embedded in a flat dielectric (2), except for the connector for the high-voltage source, wherein the dielectric (2) forms an upper surface (1) and a lower surface (4) which (Continued)

appears as a flat surface to the surface to be treated, enables the drainage or supply of a fluid by means of a simple design. The flat electrode (14) has through openings (15) distributed across the surface thereof, and the dielectric (2) is provided with through openings (3) which extend from the lower surface (4) to the upper surface (1) and which align with the through openings (15) of the electrode (14) and which have smaller dimensions than the through openings (15) of the electrode (14), so that the dielectric (2) is also completely covered in the region of the through openings (15) of the electrode (14).

9 Claims, 10 Drawing Sheets

(51) Int. Cl.
    *A61L 2/14*    (2006.01)
    *H01J 37/32*    (2006.01)
    *H05H 1/24*    (2006.01)
    *A61B 18/00*    (2006.01)
    *A61B 18/14*    (2006.01)

(52) U.S. Cl.
    CPC .. *H01J 37/32348* (2013.01); *H01J 37/32541* (2013.01); *H01J 37/32568* (2013.01); *H05H 1/2406* (2013.01); *A61B 2018/00452* (2013.01); *A61B 2018/147* (2013.01); *A61L 2202/16* (2013.01); *H05H 2001/2418* (2013.01); *H05H 2277/10* (2013.01)

(56) References Cited

U.S. PATENT DOCUMENTS

| | | | |
|---|---|---|---|
| 2013/0345620 | A1 | 12/2013 | Zemel et al. |
| 2014/0182879 | A1* | 7/2014 | Busse ............... A61N 1/40 |
| | | | 174/98 |

FOREIGN PATENT DOCUMENTS

| | | | | |
|---|---|---|---|---|
| DE | 10 2008 030 913 | A1 | | 1/2010 |
| DE | 10 2009 047 220 | A1 | | 6/2011 |
| DE | 10 2011 001 416 | A1 | | 9/2012 |
| DE | 10 2011 105 713 | A1 | | 12/2012 |
| DE | 10 2009 060627 | B4 | | 6/2014 |
| EP | 2 160 081 | A1 | | 3/2010 |
| EP | 2323600 | A1 * | 5/2011 | ....... A61F 13/00051 |
| WO | WO-2012175066 | A1 * | 12/2012 | ............... A61N 1/40 |

* cited by examiner

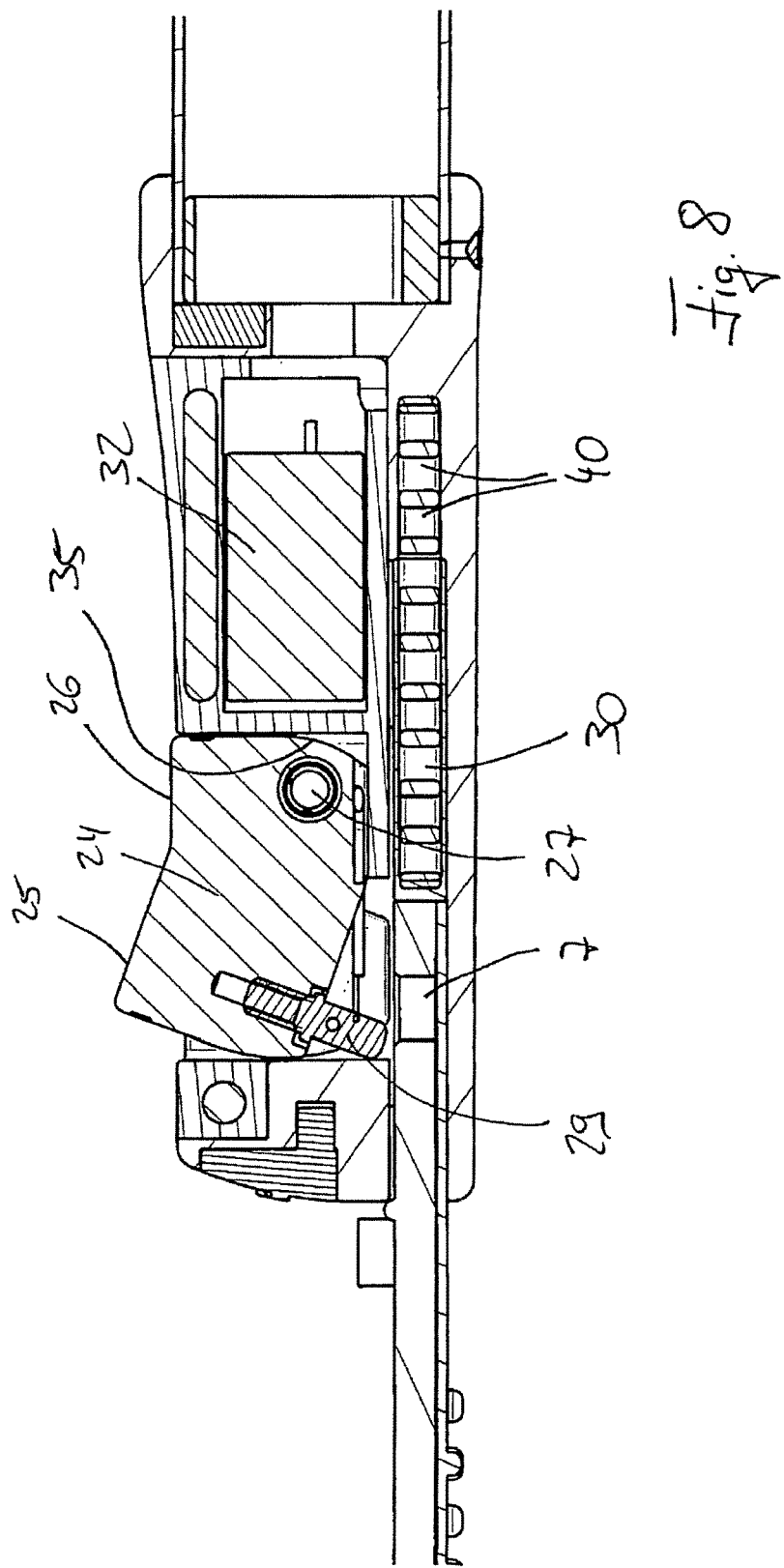

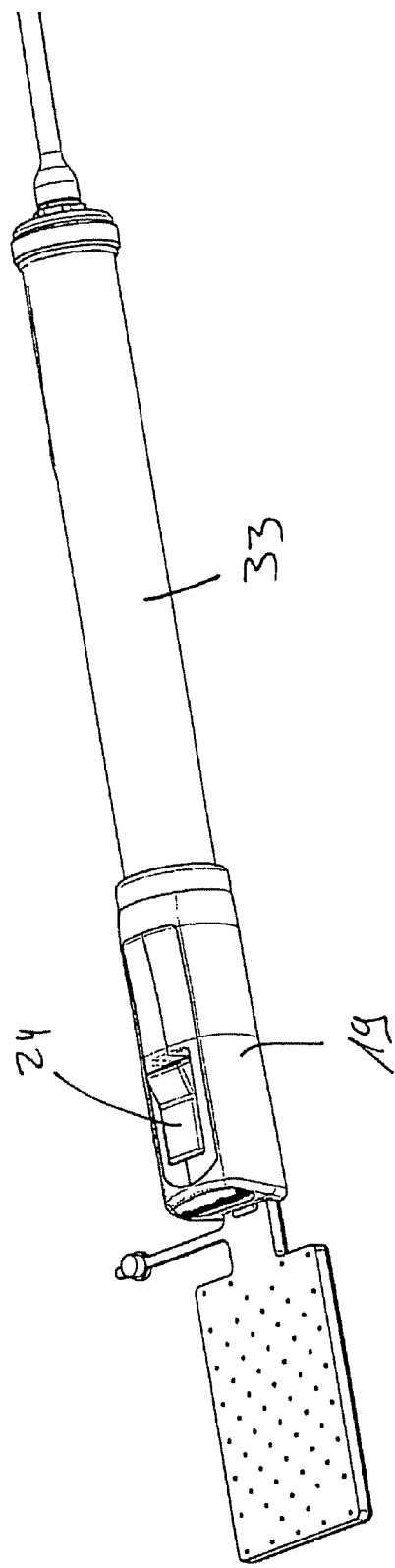

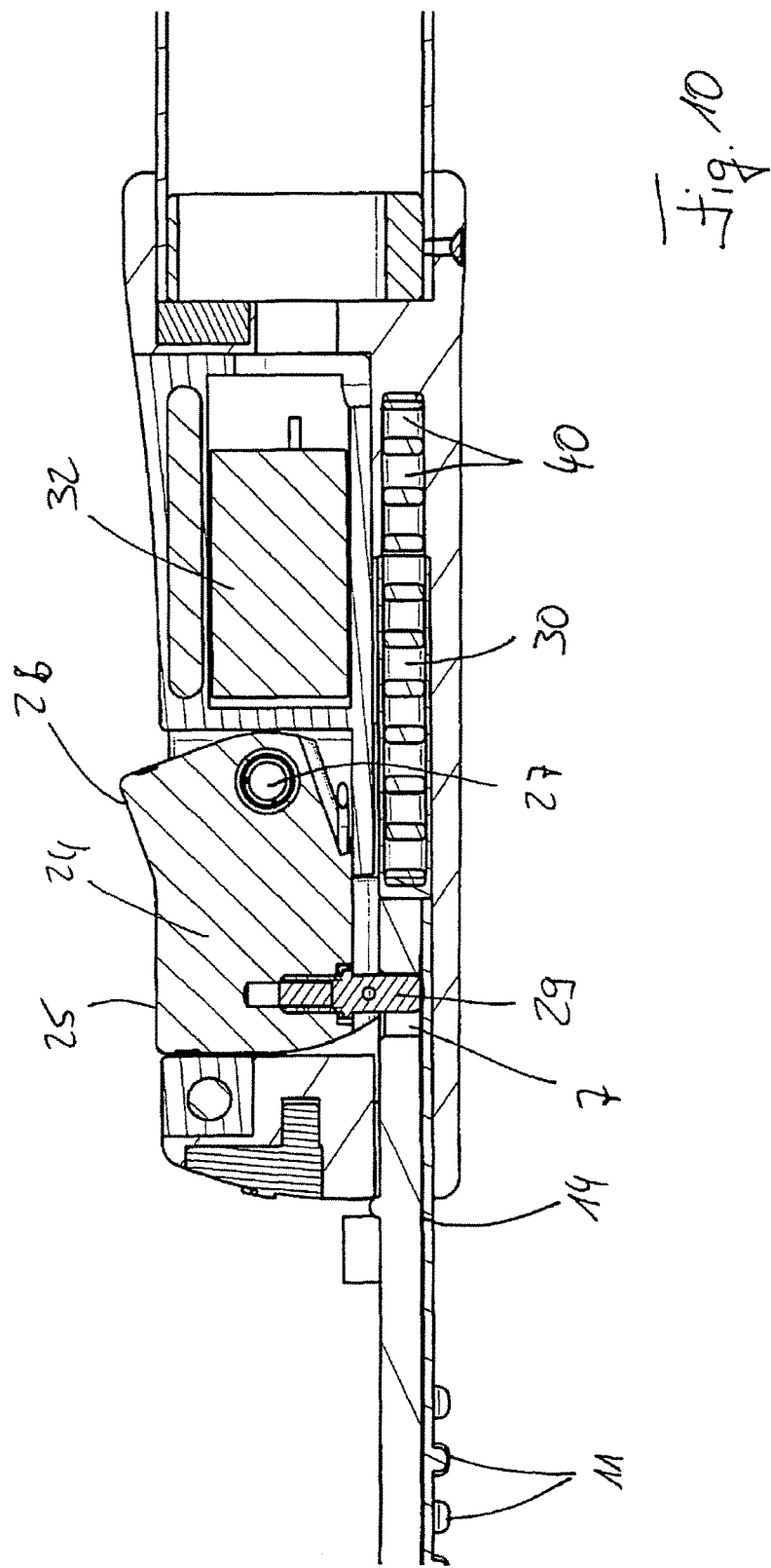

ELECTRODE ARRANGEMENT FOR FORMING A DIELECTRIC BARRIER PLASMA DISCHARGE

The invention relates to an electrode arrangement for forming a dielectric barrier plasma discharge between a flat surface of the electrode arrangement and a surface to be treated, which functions as a counterelectrode and on which a fluid can collect, comprising a flat electrode which can be connected to a high voltage source by means of a connector and which is completely embedded in a flat dielectric, except for the connector for the high voltage source, wherein the dielectric forms a top surface and a bottom surface forming a flat surface facing the surface to be treated.

Such a flat electrode arrangement which can be designed in a flexible manner is known from DE 10 2009 060 627 B4. In this case, the flat electrode is embedded between a bottom surface of a dielectric and a top surface of a dielectric, each of which extends, in the surface, beyond the electrode and therefore also covers the narrow edge of the electrode, and therefore contact with the high voltage-carrying electrode is ruled out. An approach toward the electrode which could result in a sparkover is also ruled out. Rather, the dielectric prevents a current flow from the electrode to the surface to be treated, which functions as a counterelectrode. The electrode arrangement therefore does not comprise a separate counterelectrode. In order to ensure the formation of a plasma in the air layer between the surface to be treated and the dielectric, in the case of a smooth surface to be treated, the bottom surface of the electrode arrangement, which faces the surface to be treated, can be formed having protuberances which rest, via their top surface, on the surface to be treated and have continuous intermediate spaces in which the plasma can form when a high voltage, in particular an alternating high voltage, is applied at the high voltage electrode.

Such a flat electrode arrangement can rest on the surface to be treated, wherein the surface to be treated can also be, in particular, the skin of a human or animal body. The plasma treatment results, in this case, in a pore-deep disinfection of the skin and improves the ability of the skin to absorb therapeutic substances which are applied onto the treated skin.

It is also known that a plasma treatment can be advantageous for wound healing. According to DE 10 2009 047 220 A1, a plasma is generated in a pen-like device, through which a treatment gas flows, and exits at an end face of the device, which is designed similar to a nozzle, and can be directed onto the skin or wound to be treated.

A similar device, which functions according to the same principle, is disclosed in EP 2 160 081 A1.

DE 10 2011 001 416 A1 discloses a flat, flexible wound-treatment device, in which two flat electrodes are formed by interwoven, insulated, electrical conductors. The high voltage intended for generating a plasma in the air gaps forms between the conductors. For this purpose, it is necessary for the entire electrode arrangement to be gas permeable. If an insulation of the electrode wires becomes faulty, sparkovers occur between the high voltage electrodes, which can cause severe damage on the skin surface on which the electrode arrangement rests via a wound-contact layer. The electrode arrangement permits a certain drainage of a secreted fluid from the wound surface, but the safety thereof is difficult or impossible to ensure.

The problem addressed by the present invention is that of expanding the scope of application of an electrode arrangement of the type mentioned at the outset, without having to accept a reduction in safety and without implementing complicated structures.

This problem is solved according to the invention by an electrode arrangement of the type mentioned at the outset by way of the flat electrode having through-holes distributed across its plane, and the dielectric being provided with through-holes which extend from the bottom surface to the top surface, align with the through-holes of the electrode, and have smaller dimensions than the through-holes of the electrode, whereby the dielectric completely covers the electrode also in the region of the through-holes.

The electrode arrangement according to the invention is designed, in principle, similar to the electrode arrangement known from DE 10 2009 060 627 B4 and can likewise implement all the advantages associated therewith. According to the invention, the electrode arrangement is designed in such a way, however, that the electrode arrangement does consist of flat, connected parts, namely the flat, connected electrode and the flat, connected dielectric, on the one hand, but a fluid can still be drained, through the through-holes of the dielectric, out of the intermediate space between the bottom surface of the dielectric and the surface to be treated, without having to accept a reduction in the safety of the electrode as a result. Rather, the dielectric forms small channels which extend from the bottom surface to the top surface and are delimited on all sides by a sufficiently thick dielectric layer, and so there is no danger of direct contact with the high voltage-carrying electrode. According to the invention, the flat body of the electrode arrangement itself is therefore suitable for draining fluid through the channels, and therefore no special arrangement needs to be provided for draining fluid, in particular wound secretions and any resultant gases.

In one preferred embodiment, the electrode arrangement according to the invention can also comprise a bottom surface of the dielectric, which is provided with protuberances, wherein the protuberances define a height of an open space when the protuberances rest on the surface to be treated. The open space is at least partially utilized for forming a plasma in a gas, for example, air, which is located in the open space. The through-holes are preferably located between the protuberances. At least some of the through-holes can also extend through the protuberances, however.

The dielectric preferably consists of a castable plastic. In this case, it is possible that the dielectric embedding the electrode is produced as one piece by encapsulating the electrode. In terms of tools, it is simpler, however, when the dielectric is produced as two pieces, namely from a bottom surface and a top surface, wherein the electrode is inserted into the bottom surface or the top surface and then the dielectric is closed by placing the other part thereon and connecting the two parts together. This connection can be established by way of injecting the second part onto the first part, into which the electrode has already been placed, so that an integrally joined connection results. In addition, it is possible to connect the two parts of the dielectric together by means of welding or bonding.

In one preferred embodiment, the connector of the electrode free from the dielectric is connected to a contact arrangement which engages over the connector in a clamping and insulating manner. In this case, the contact arrangement can preferably have a clamping state and an initial state, wherein, in the clamping state, a high voltage contact presses with a preload against the connector of the electrode and, in the initial state, the high voltage contact can be covered by an insulating piece which is movable with the transition from the initial state into the clamping state. In this case, it is particularly advantageous if the contact arrangement comprises a housing having a slot, which is open on one side, for the connector of the electrode, and if a clamping arrangement for pressing the high voltage contact against the connector of the electrode is mounted in the housing.

The high voltage contact is covered by the movable insulating piece in the initial state, and therefore an inadvertent contacting of a body part with the high voltage contact is not possible. For this purpose, the movable insulating piece must first be pushed away from the high voltage contact.

The high voltage contact is preferably a cylindrical contact which engages into a recess of the dielectric, which extends up to a flat connector piece of the electrode. The flat connector piece is preferably designed to be tongue-shaped and is enclosed by the dieletric, except for the recess, and therefore the movable insulating piece of the contact arrangement can be displaced by means of the tongue-shaped connector piece in order to then be capable of pressing the high voltage contact into the recess of the dielectric and, therefore, against the conducting surface of the connector piece of the electrode.

The electrode arrangement according to the invention is suited, in particular, for use as a wound dressing and, therefore, is preferably designed to be flexible overall, which is to say, having a flexible dielectric and a flexible electrode. In this case, it is advantageous if the bottom surface of the dielectric is covered with a layer which is suitable as a wound dressing. This layer should not prevent the formation of the plasma between the bottom surface of the dielectric and the surface to be treated, which is in the form of a wound in this case. Typical gauze cellulose and other dressings are therefore conceivable as wound dressing. It is particularly preferred if a layer of a solid, open-pored matrix made from a therapeutic or curative material is disposed on the surface of the dielectric. The layer can be epitaxially grown directly onto the dielectric. Alternatively, it is possible to design the layer as a separate layer, wherein the bottom surface of the dielectric is advantageously structured and the separate layer is formed having a structuring which is complementary to the structured surface of the dielectric. The structuring of the surface of the dielectric can be formed by the protuberances. The layer forming the matrix can consist of a material which can be resorbed by the body. Collagen is a preferred material. The thickness of the layer can correspond to the length of the protuberances in this case, since the plasma can also form within the layer.

The invention is described in greater detail in the following with reference to an exemplary embodiment represented in the drawing. In the drawings:

FIG. 8 shows an enlarged, cut representation of the state according to FIG. 7;

FIG. 9 shows a representation according to FIG. 7, although with the contact arrangement in a state locked on a connector piece of the electrode, in a press-down position of the preload contact; and FIG. 10 shows an enlarged and cut representation of the state according to FIG. 9.

Figure 1:
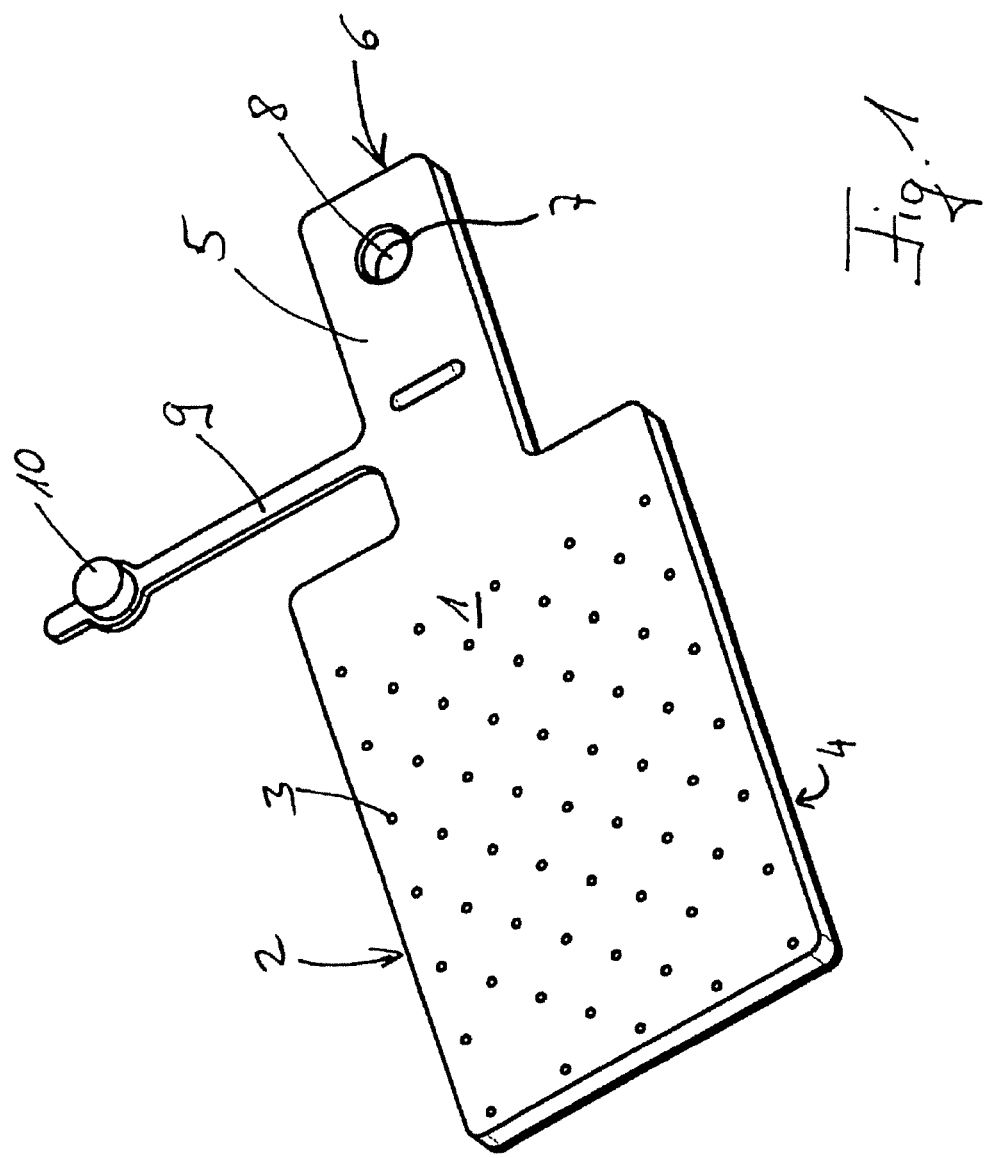
FIG. 1 shows a perspective view of the top surface of an electrode arrangement according to the invention.

The electrode arrangement represented in FIG. 1 has a top surface 1 of a dielectric 2, across which the numerous through-holes 3 are distributed. The through-holes 3 are shown in FIG. 1 distributed in a uniform pattern. This is advantageous, although not absolutely necessary, for a steady drainage of fluid from a surface to be treated. For particular applications, it can be advantageous to provide a non-uniform distribution of the through-holes 3 across the dielectric, for example, a greater density of the through-holes 3 in the center of the flat electrode arrangement than at the edge.

The dielectric 2 has a low height relative to the surface of the top surface 1 and the through-holes 3 extend, perpendicularly to the top surface 1, from the top surface 1 to a bottom surface 4 which is not represented in FIG. 1, and therefore have a channel length which corresponds to the height of the dielectric 2. The electrode arrangement of the represented exemplary embodiment consists of an essentially rectangular surface. This shape is not absolutely necessary, however, and can be adapted to the particular application. It is likewise conceivable that the surface of the electrode arrangement provided with the through-holes 3 is oval, circular, or angled. The electrode arrangement and the dielectric 2 comprise a tongue-shaped connector piece 5 which is designed as a narrow, rectangular web and has, on a front free end 6 thereof, a cylindrical recess 7 in the dielectric 2. One part of a conductive connector piece 8 is exposed at the base of the recess 7.

A cylindrical stopper 10 is integrally connected to the dielectric 2, to the tongue-shaped connector piece 5 of the dielectric 2, via a narrow, strip-shaped projection 9. The stopper 10 is used for closing the cylindrical recess 7 in order to protect the conductive surface of the conductive connector piece 8 against contamination.

Figure 2:
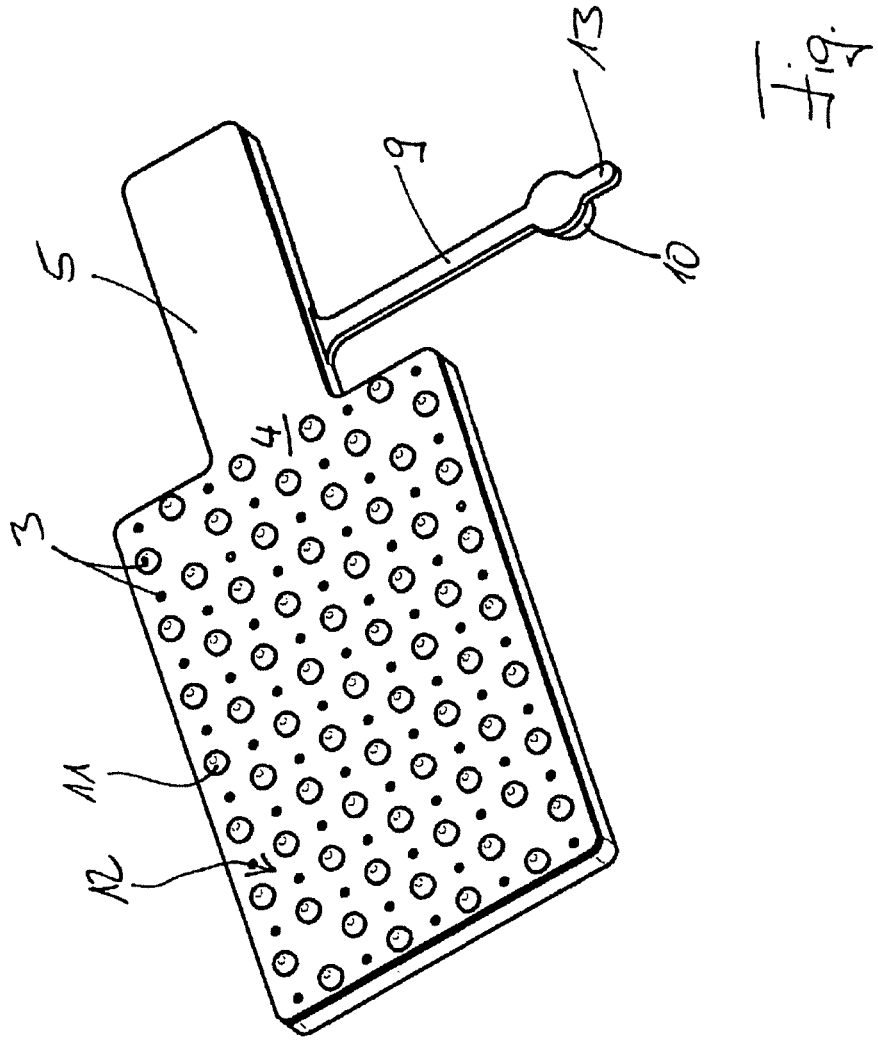
FIG. 2 shows a perspective view of a bottom surface of an electrode arrangement according to the invention.

FIG. 2 shows the corresponding bottom surface 4 of the dielectric 2. The free mouth openings of the through-holes 3 are apparent on the bottom surface 4. In addition, the bottom surface 4 is provided with a multiplicity of protuberances 11 which form a contiguous open space 12 between themselves when the protuberances rest on a surface to be treated. In this case, the protuberances 11 ensure that a sufficient quantity of gas or air is located in the open space, in which the intended plasma can form.

FIG. 2 also shows that the stopper 10 is provided with an overhanging tab 13 which aligns with the strip-shaped projection 9 and by means of which the stopper can be pulled out of the cylindrical recess 7 when the electrode arrangement is intended to be operated.

Figure 3:
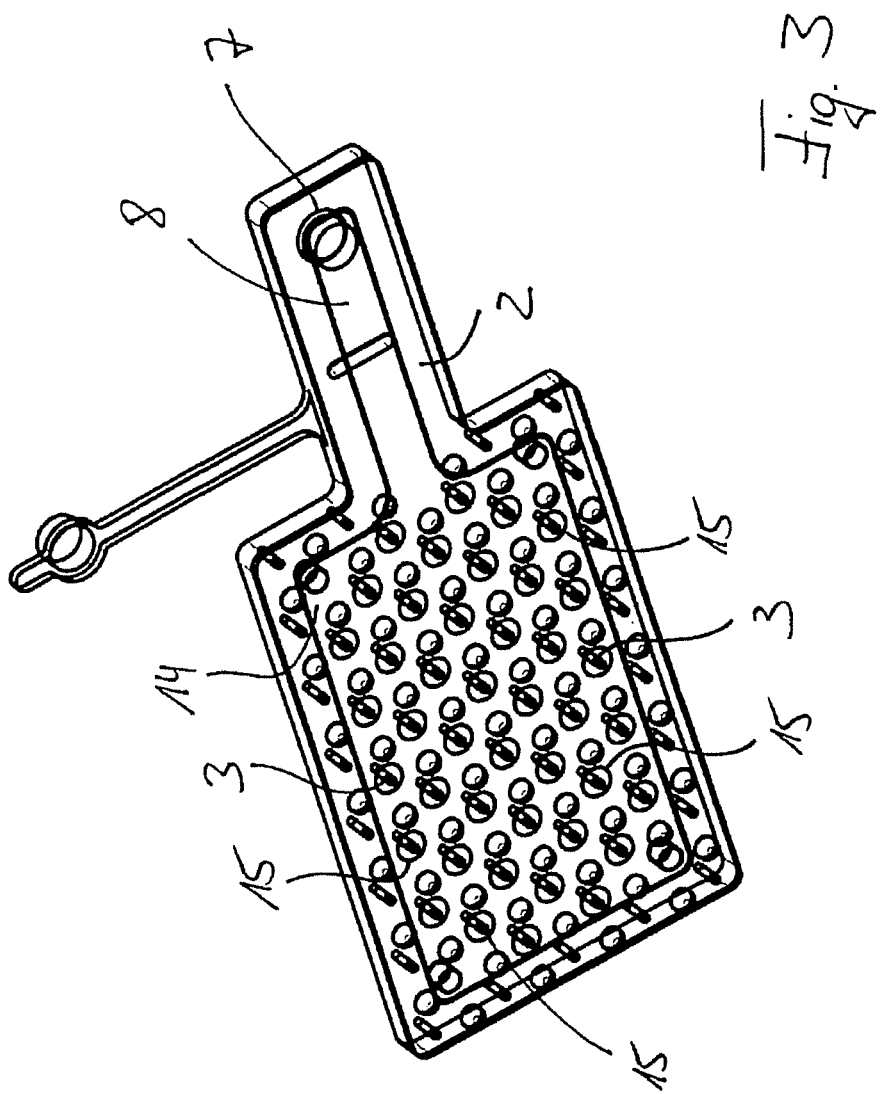
FIG. 3 shows a representation of the electrode within the electrode arrangement including a dashed-line representation of the dielectric for illustrating the embedding of the electrode.

FIG. 3 shows that a flat, flexible electrode 14 is embedded in the dielectric 2 and essentially has the shape of the dielectric 2, although having smaller dimensions on all sides, and therefore the dielectric 2 surrounds the electrode 14 in an insulating manner on all sides. The electrode 14 consists of a flat, flexible, conductive material. The flexibility can result from an elastic deformability or from a plastic deformability of the material of the electrode 14. The electrode 14 is provided with through-holes 15 in the essentially rectangular region, which align with the through-holes 3 of the dielectric 2 but have substantially larger dimensions. The dielectric 2 is designed in such a way that it extends through the through-holes 15 and therefore forms tubular channels in the through-holes 15, which are delimited exclusively by a sufficient wall thickness of the dielectric 2. In this way, a fluid can pass through the through-holes 3 of the dielectric 2 without coming into direct contact or into too close proximity of the material of the electrode 14.

The electrode 14 is integrally connected to the connector piece 8 which extends, likewise in a tongue-shaped manner, into the tongue-shaped connector piece 5 to such an extent that it can form the base of the cylindrical recess 7. In this way, the electrode can be contacted through the cylindrical recess 7.

The dielectric 2 can integrally surround the electrode 14 by way of the electrode being enclosed by the dielectric on all sides by injection or casting, in an injection process.

Figure 4:
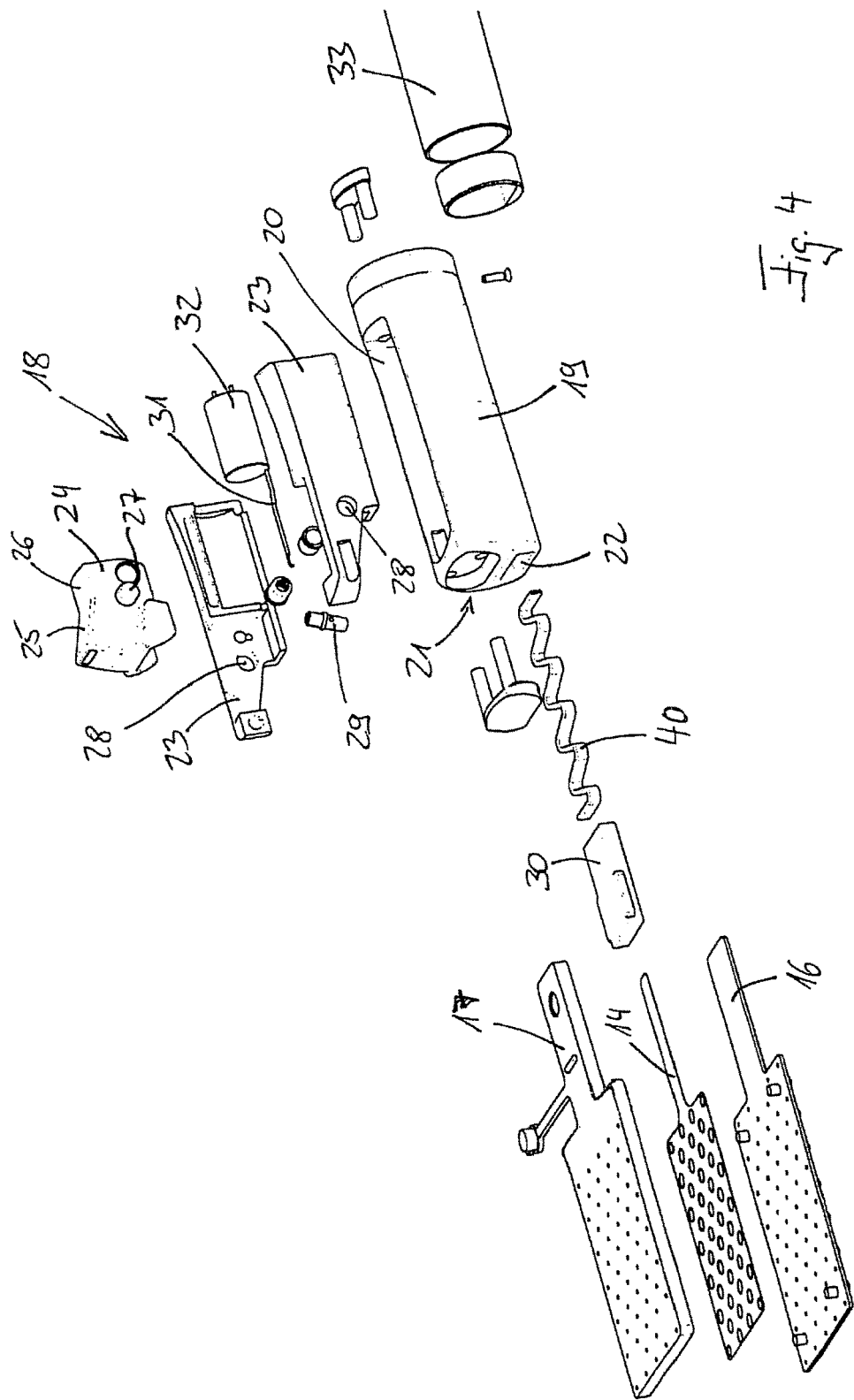
FIG. 4 shows a representation of the parts of the electrode arrangement, including a contact arrangement.

FIG. 4 shows, however, that it can be advantageous in terms of simplifying the injection mold if the dielectric is produced from an top part 16 and a bottom part 17. In this case, the electrode 14 can be placed into the tub-shaped top part 16. Next, the bottom part 17 is placed thereon and is connected to the top part preferably in an integrally joined manner, whether it be by bonding or welding. It is also possible to place the top part 16, including the inserted electrode, into an injection mold for the bottom part 17 and to then form the bottom part, wherein said bottom part forms a unified component having the same material as the top part 16. The process can be reversed, of course, and the electrode can be initially placed into a tub-shaped or suitably shaped bottom part 17 before the top part 16 is placed thereon and is connected to the bottom part 17.

High voltage is supplied to the electrode 14 via the surface of the connector piece 8 of the electrode 14, which forms the base of the cylindrical recess 7, by means of a contact arrangement 18, the individual parts of which are represented in FIG. 4. The contact arrangement 18 comprises a tubular housing 19 which forms a chamber 20 which is open toward the top. A free front end face 21 of the housing is provided with an insertion slot 22, through which the tongue-shaped connector piece 5 of the dielectric 2 can be inserted into the chamber 20. Two lateral pieces 23 can be inserted into the chamber 20, between which a rocker switch 24 is mounted. The rocker switch 24 has, on the top side thereof and in a known manner, two actuation surfaces 25, 26 situated at an angle with respect to one another. Two cylindrical axle stubs 27 protrude from the side walls of the rocker switch, which can be inserted into corresponding circular recesses 28 and enable the rotatable movement of the rocker switch 24. Connected to the rocker switch is a cylindrical high voltage contact 29 which protrudes downward from the rocker switch and can be covered toward the bottom by a displaceable insulating plate 30. The displaceable insulating plate 30 is guided in corresponding (non-illustrated) guides of the lateral pieces 23 and is acted upon toward the left, as shown in FIG. 4, with a force from a compression spring 40.

The high voltage contact 29 is connected, in the rocker switch 24, to an output line 31 of a high voltage transformer 32 which transforms a high-voltage alternating voltage from mains alternating voltage supplied to said transformer.

The rear end face of the housing 19 is open and is connected to a protective cable casing 33, by means of which a mains line can be connected to the high voltage transformer 32 disposed in the chamber 20, at the back end thereof.

Figure 5:
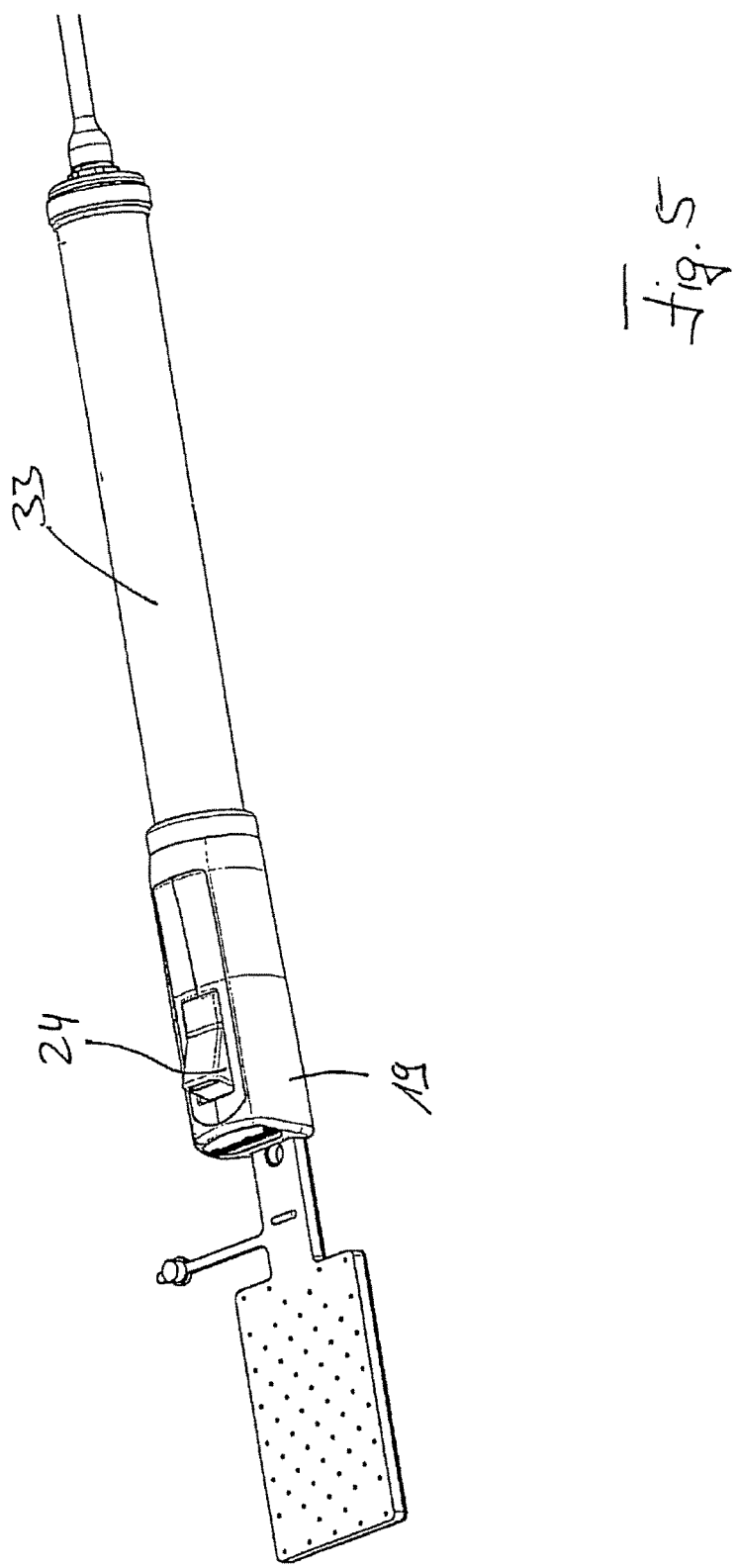
FIG. 5 shows a perspective schematic representation, wherein a tongue-shaped connector piece of the electrode arrangement has not yet been inserted into the contact arrangement.
Figure 6:
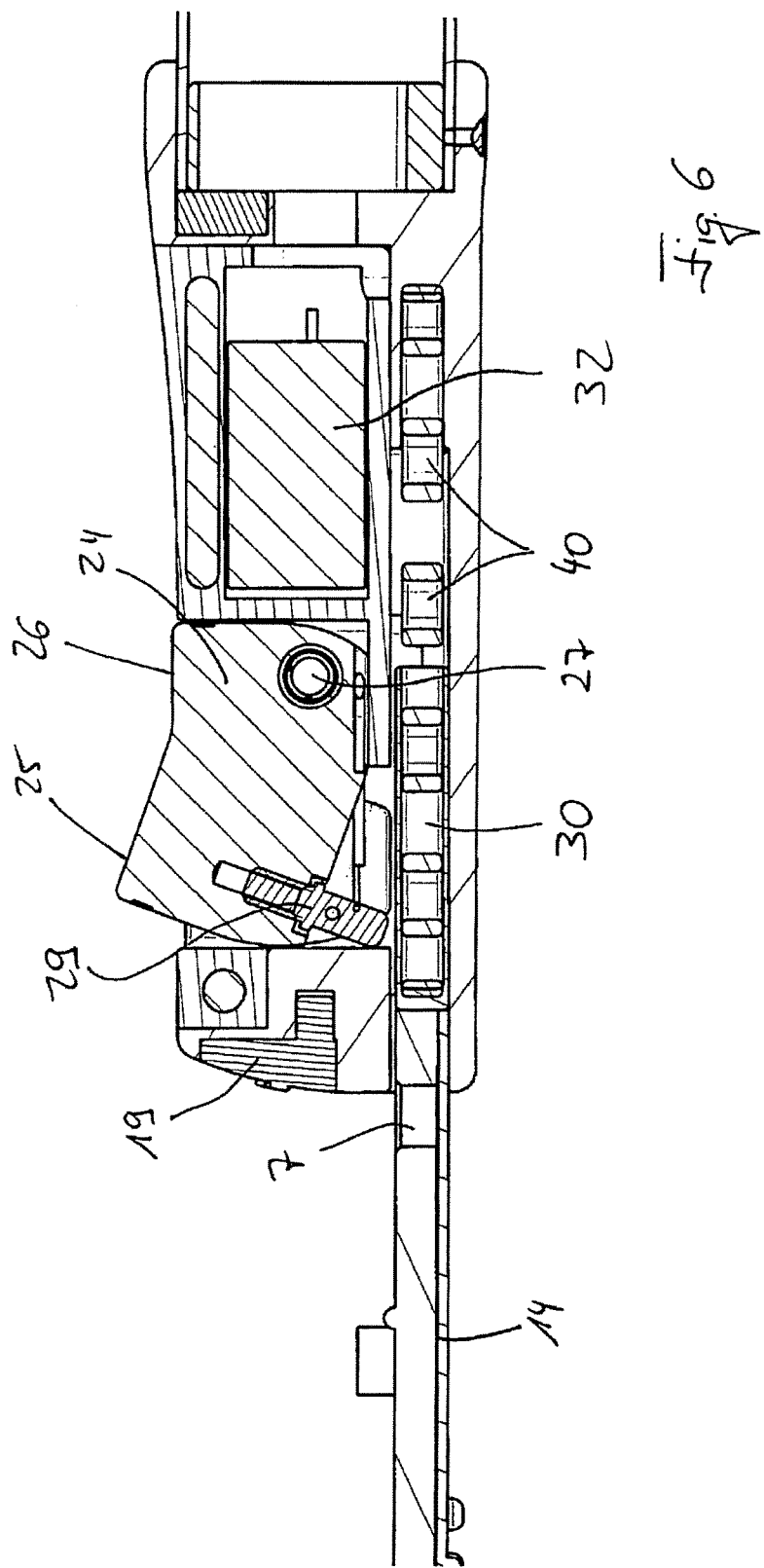
FIG. 6 shows an enlarged, cut representation of the contact arrangement in the state according to FIG. 5.

FIGS. 5 and 6 show an initial state of the contact arrangement, in which the displaceable insulating plate 30 is located on the free end of the housing 19, directly behind the insertion slot 22, and therefore projection pieces 34 of the rocker switch 24 are supported on the insulating plate and prevent an actuation of the rocker switch 24 on the front actuation surface 25. In this state, the cylindrical high voltage contact 29 also rests on the displaceable insulating plate 30.

Figure 7:
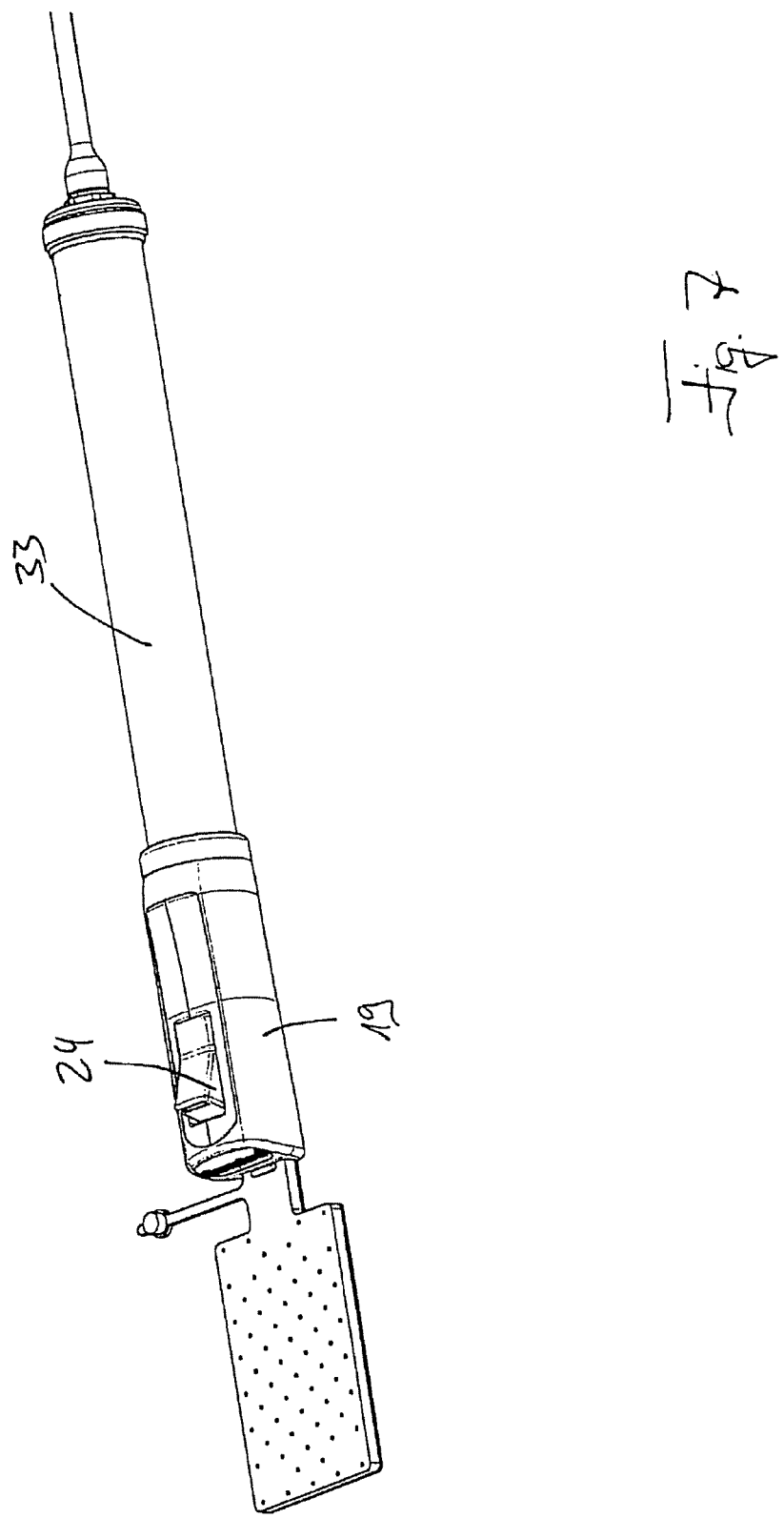
FIG. 7 shows the representation according to FIG. 5, although with the connector piece of the electrode arrangement inserted.

FIGS. 7 and 8 show an intermediate state, in which the tongue-shaped connector piece 5 of the dielectric 2 has been inserted into the insertion slot 22 of the housing 19 of the contact arrangement 18. As a result, the displaceable insulating plate 30 has now been slid toward the back and has exposed the high voltage contact 29 which now glides on the top surface 1 of the connector piece 5 of the dielectric 2 until it comes to rest over the cylindrical recess 7. In this state, the rocker switch 24 can be pressed downward by pressing onto the front actuation surface 25 on the front end thereof, so that the high voltage contact 29 moves into the cylindrical recess 7 and comes to rest, via its front end face, against the top surface of the connector piece 8 of the electrode 14. FIG. 8 shows that the rocker switch 24 has a rear, cam-shaped terminal wall 35 which, together with a vertical housing intermediate wall 36, permits a movement of the rocker switch 24 beyond a resistance and into a locked clamped position when the rocker switch 24 is pressed downward via the front actuation surface 25 and rotates about the axle stubs 27.

FIGS. 9 and 10 show a clamping state of the contact arrangement 18, in which the front actuation surface 25 now lies horizontal and the rear actuation surface extends slightly upward. In the clamping state of the contact arrangement 18 represented in FIGS. 9 and 10, the high voltage contact 29 contacts the electrode 14 at its tongue-shaped connector piece 8, and therefore, in this state, the electrode 14 is supplied with the high voltage generated by the high voltage transformer 32.

In the exemplary embodiment shown, the high voltage is generated by the high voltage transformer 32 in the housing 19 of the contacting arrangement 18, in order to keep the paths for the high voltage line short and reliably insulated. It is also possible, of course, to generate the high voltage outside of the housing 19 and to conduct said voltage into the housing, via a sufficiently insulated and protected feed cable, to the high voltage contact 29.

The present invention is furthermore not limited to the exemplary embodiment shown. In particular, for the treatment of certain surfaces, it is not necessary to provide a bottom surface 4 of the dielectric 2 with protuberances 11.

The number of through-holes 3 in the dielectric 2, via which gases as well as fluids are drained and, as necessary, fresh air or treatment gases can be introduced into a wound region, can be greatly varied depending on the particular application. The number can therefore readily fluctuate between 2 and 100, depending on the size of the electrode arrangement and according to the particular application. It is apparent to a person skilled in the art that a larger number of through-holes 3 can also be implemented and, as necessary, is indicated for larger electrode arrangements.

The contact arrangement 18 shown is advantageous for the high voltage contacting of the electrode, although the contact arrangement can be subject to numerous design variations. Furthermore, it is entirely possible to also provide the electrode 14 with a connector piece 5 which protrudes entirely from the dielectric 2. Alternatively, it is also possible to design the dielectric without a recess 7 and, instead, to design one or more high voltage contacts 29 to be cutting, so that the high voltage contacting cuts through the dielectric 2 until it comes to rest on the top surface of the electrode 14. Further design variants can be implemented within the scope of the invention.

The electrode arrangement according to the invention is suited for placement directly on human skin and, in particular, on flat wounds. For this particular application, it is particularly advantageous to provide the dielectric, on the bottom surface thereof, with a layer of a skin-friendly and skin-benefiting material. This layer can be applied on the dielectric for epitaxial growth, so that the layer is connected to the dielectric 2. The layer can also be produced as a separate part, however, and can be connected to the bottom surface 4 of the dielectric 2. All types of wound dressings are conceivable in this case. A layer made from a solid, open-pore matrix made from a therapeutic or curative material, for example, collagen, is preferred in this case.

The invention claimed is:

1. An electrode arrangement, comprising:
   a flat electrode connectable to a high voltage source by a connector; and
   a flat dielectric, wherein the flat electrode except for the connector for the high voltage source is completely embedded in the flat dielectric, wherein the flat dielectric has a top surface and a bottom surface, wherein the bottom surface is a flat surface which faces a surface to be treated,
   wherein the flat electrode has through-holes distributed over a plane formed by the flat electrode, and the flat dielectric has through-holes which extend from the bottom surface to the top surface and align with the through-holes of the flat electrode,
   wherein the through-holes of the flat dielectric have smaller dimensions than the through-holes of the flat electrode but where the smaller dimensions are sufficient to allow fluid to pass therethrough from the bottom surface to the top surface of the flat dielectric, and
   wherein the flat dielectric completely covers the flat electrode in each of the through-holes in the flat electrode,
   wherein the bottom surface of the flat dielectric includes one or more features projecting therefrom which define a height of an open space when the electrode arrangement rests on the surface to be treated,
   wherein the electrode arrangement is configured for forming a dielectric barrier plasma discharge in the open space between the bottom surface of the electrode arrangement and the surface to be treated with the surface to be treated functioning as a counter electrode, and with the fluid that collects on the surface to be treated being permitted to pass through the through-holes of the flat dielectric without contacting the through-holes of the flat electrode.

2. The electrode arrangement as claimed in claim 1, wherein the one or more features are circular protuberances.

3. The electrode arrangement as claimed in claim 2, wherein the through-holes of the flat dielectric are located between the protuberances.

4. The electrode arrangement as claimed in claim 1 wherein the flat dielectric consists of a castable plastic.

5. A combination of a contact arrangement and an electrode arrangement,
   wherein the electrode arrangement comprises
   a flat electrode connectable to a high voltage source by a connector; and
   a flat dielectric, wherein the flat electrode except for the connector for the high voltage source is completely embedded in the flat dielectric, wherein the flat dielectric has a top surface and a bottom surface, wherein the bottom surface is a flat surface which faces a surface to be treated,
   wherein the flat electrode has through-holes distributed over a plane formed by the flat electrode, and the flat dielectric has through-holes which extend from the bottom surface to the top surface and align with the through-holes of the flat electrode,
   wherein the through-holes of the flat dielectric have smaller dimensions than the through-holes of the flat electrode but where the smaller dimensions are sufficient to allow fluid to pass therethrough from the bottom surface to the top surface of the flat dielectric, and
   wherein the flat dielectric completely covers the flat electrode in each of the through-holes in the flat electrode, and
   wherein the bottom surface of the flat dielectric includes one or more features projecting therefrom which define a height of an open space when the electrode arrangement rests on the surface to be treated,
   wherein the electrode arrangement is configured for forming a dielectric barrier plasma discharge in the open space between the bottom surface of the electrode arrangement and the surface to be treated with the surface to be treated functioning as a counter electrode, and with the fluid that collects on the surface to be treated being permitted to pass through the through-holes of the flat dielectric without contacting the through-holes of the flat electrode, and
   wherein the electrode arrangement is connectable to the contact arrangement with the connector of the flat electrode which is free from the flat dielectric being configured to be connected to the contact arrangement which engages over the connector in a clamping and insulating manner, wherein
   the contact arrangement has a clamping state and an initial state, wherein a high voltage contact presses with a preload against the connector of the flat electrode in the clamping state and, in an initial state, the high voltage contact is covered by an insulating piece which is movable with a transition from the initial state into the clamping state.

6. The combination as claimed in claim 5, wherein the contact arrangement comprises a housing having a slot which is open on one side, and a clamping arrangement for pressing the high voltage contact against the connector of the electrode, wherein the clamping arrangement is mounted in the housing.

7. The combination as claimed in claim 5 wherein the high voltage contact is a cylindrical contact which engages into a corresponding recess of the flat dielectric in the clamping state, and the recess extends up to a flat connector piece of the flat electrode.

8. The electrode arrangement as claimed in claim 1 wherein the bottom side of the flat dielectric is coated with a wound dressing.

9. The electrode arrangement as claimed in claim 8, wherein the wound dressing consists of a layer made from a solid, open-pore matrix made from a therapeutic or curative material.

\* \* \* \* \*